(12) United States Patent
Girshin et al.

(10) Patent No.: US 8,348,854 B2
(45) Date of Patent: Jan. 8, 2013

(54) END-TIDAL $CO_2$ MONITORING TUBE HOLDER

(76) Inventors: Michael Girshin, New York, NY (US); Roni Mendonca, New Rochelle, NY (US)

( * ) Notice: Subject to any disclaimer, the term of this patent is extended or adjusted under 35 U.S.C. 154(b) by 1089 days.

(21) Appl. No.: 12/233,394

(22) Filed: Sep. 18, 2008

(65) Prior Publication Data
US 2010/0069770 A1    Mar. 18, 2010

(51) Int. Cl.
*A61B 5/08* (2006.01)
*A61M 15/08* (2006.01)
(52) U.S. Cl. .................... 600/532; 128/207.18
(58) Field of Classification Search .......... None
See application file for complete search history.

(56) References Cited

U.S. PATENT DOCUMENTS

| | | | | |
|---|---|---|---|---|
| 5,097,827 A | * | 3/1992 | Izumi | 128/207.18 |
| 5,336,179 A | * | 8/1994 | Ryan | 604/80 |
| 2005/0277888 A1 | * | 12/2005 | Propp | 604/174 |

* cited by examiner

*Primary Examiner* — Shanon A Foley
(74) *Attorney, Agent, or Firm* — Greenberg Traurig, LLP; Roman Fayerberg; David J. Dykeman

(57) ABSTRACT

Devices for attaching medical tubing to a nasal cannula are provided. Such devices may comprise a body having a distal end and a proximal end, a connector disposed on the body and adapted to releasably attach the body to the nasal cannula, and one of the following: at least one tube holding member extending along at least one surface of the body and adapted to accept the medical tubing, or at least one body channel extending through the body and having an outlet at the distal end of the body, and a tube connector attached to the proximal end of the body and adapted to fluidly connect the medical tubing the at least one channel.

8 Claims, 4 Drawing Sheets

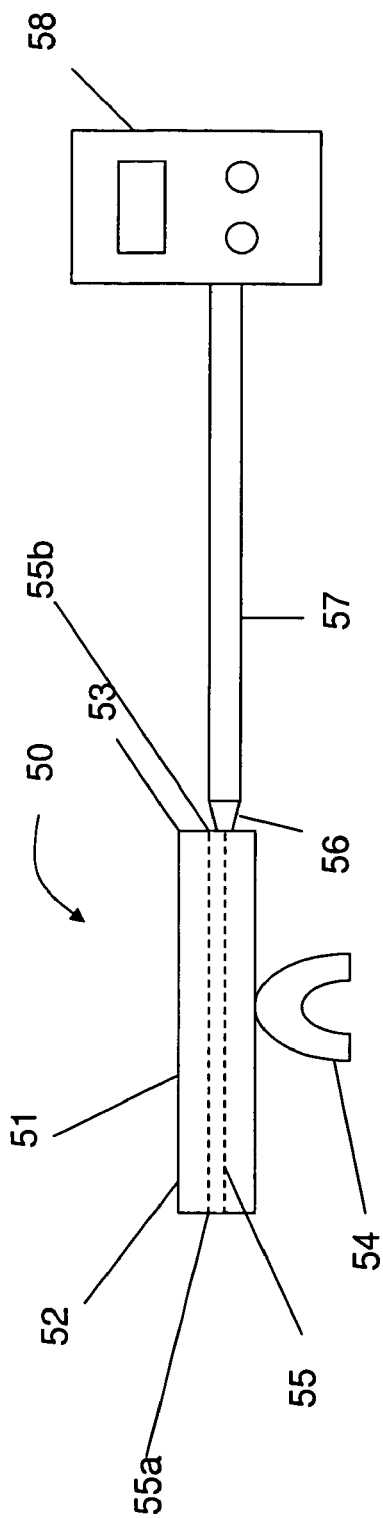
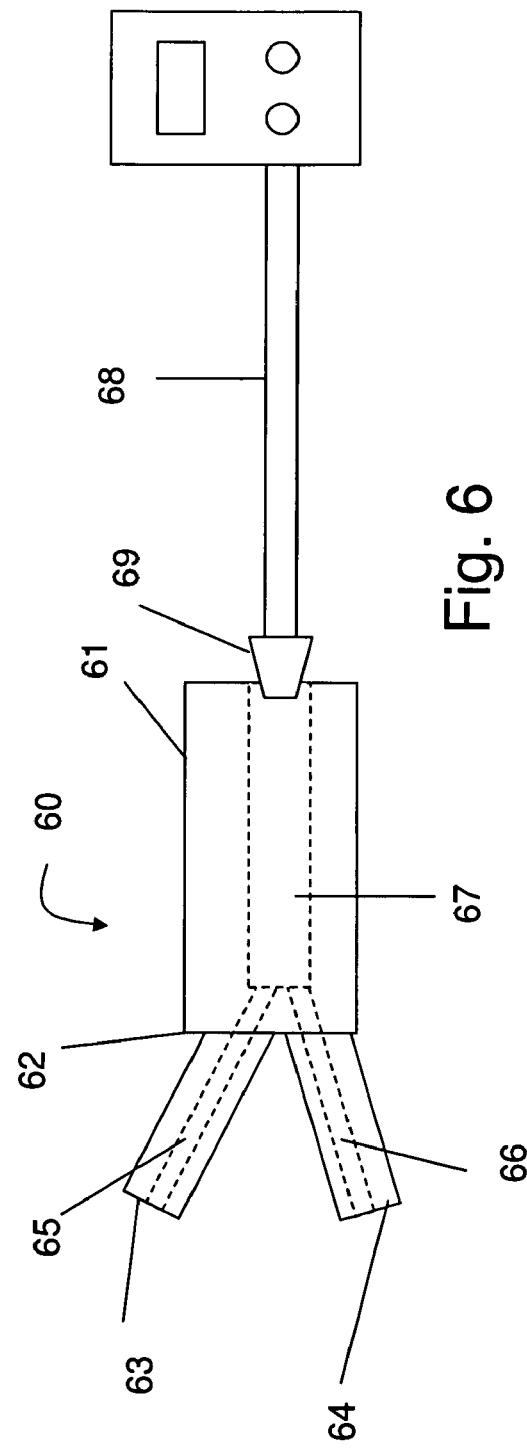
Fig. 5
Fig. 6

US 8,348,854 B2

END-TIDAL CO₂ MONITORING TUBE HOLDER

FIELD OF THE INVENTION

This invention relates to a device for attaching medical tubing to a nasal cannula.

BACKGROUND OF THE INVENTION

Anaesthesia allows patients to undergo surgery and other procedures without the distress and pain they would otherwise experience. A variety of drugs, referred herein as anesthetic drugs, may be given to a patient to block sensation in the patient by ensuring patient's unconsciousness, amnesia, analgesia and paralysis during the surgery and for some time after surgery. The anesthetic drugs may be administered by a variety of routes, including by injection or by inhalation. To administer the anesthetic drugs by inhalation, the following steps are typically taken: the drugs are formulated to evaporate easily, the vapors of the anesthetic drugs are mixed with carrier gasses, such as oxygen or nitrous oxide, and the mixture is administered to a patient throughout the surgery from an anesthesia machine. During sedation, oxygen is administered to the patient via medical tubing connected to a nasal cannula.

During surgery, patients being administered anesthetic drugs are continuously monitored to ensure the patient's safety. One of the standard monitoring tools is a capnograph, which monitors the carbon dioxide ($CO_2$) in the exhaled respiratory gases. Monitoring amount of $CO_2$ in exhaled respiratory gasses, which is known as Capnography, provides one of the most rapid and reliable methods to detect life-threatening conditions, including movement of tracheal tubes, unsuspected ventilatory failure, circulatory failure and defective breathing circuits, and enables physician to circumvent potentially irreversible patient injury.

Some nasal cannulas may also include a built-in means for sampling exhaled respiratory gases for $CO_2$. Such cannulas are, however, extremely expensive and cannot be afforded by many hospitals. Alternatively, a medical tubing connected to a capnograph may be simply positioned near a patient's nose by, for example, attaching the medical tubing to a nasal cannula, such as by tape. This method, although easy and inexpensive, suffers from a number of shortcomings. For example, the connection between the medical tubing and the cannula may be insufficiently firm so the medical tube may shift from the desired position during the surgery. In addition, taping the medical tubing may result in pinching the medical tube causing the flow through the medical tube to substantially decrease or, in some instances, to cease completely. Finally, this method of attaching medical tubing to a nasal cannula may also interfere with the position and operation of the nasal cannula itself.

Accordingly, there is still a need for a device for attaching medical tubing to a nasal cannula that ensures that the medical tubing stays in the desired position throughout the surgery without interfering with performance of the medical tubing or the nasal cannula.

SUMMARY OF THE INVENTION

The present invention fills the foregoing need by providing devices and systems for attaching medical tubing to a nasal cannula.

Accordingly, in one aspect, a End-Tidal $CO_2$ monitoring tube holder for attaching medical tubing to a nasal cannula, referred herein as a tube holder is provided.

In one embodiment, the tube holder may comprise a body having a distal end and a proximal end, a connector disposed on the body and adapted to releasably attach the body to the nasal cannula, and at least one tube holding member extending along at least one side of the body and adapted to accept the medical tubing. The connector may comprise an elongated member and a pivot that acts engage the elongated member with the body, at least one strap, or at least one elastically biased clip, or combinations thereof. The tube holding member may comprise a receptacle set in a surface of the body, at least one loop positioned along a surface of the body, or an adhesive strip positioned along a surface of the body.

In some embodiments, the body may be bifurcated at the distal end into a first prong and a second prong spaced apart form the first prong, wherein the first prong comprises at least one first tube extension member extending along at least one side of the first prong, and wherein the second prong comprises at least one second tube extension member extending along at least one side of the second prong. The first prong and the second prong may be spaced apart so the prongs are positioned in or near alternate nostrils of a patient.

In another embodiment, the tube holder may comprise a body having a distal end and a proximal end, a connector disposed on the body and adapted to releasably attach the body to the nasal cannula, at least one body channel extending through the body, and a tube connector attached to the proximal end of the body and adapted to fluidly connect the medical tubing to the at least one channel. The connector may comprise an elongated member and a pivot that acts to engage the elongated member with the body, at least one strap, or at least one elastically biased clip.

In some embodiments, the body of the tube holder may be bifurcated at the distal end into a first prong and a second prong spaced apart from the first prong, wherein the first prong comprises at least one first channel extending through the first prong and fluidly connected to the body channel and the second prong comprises a second channel extending through the second prong and fluidly connected to the body channel. The first prong and the second prong positioned in or near alternate nostrils of a patient.

In yet another aspect, systems for monitoring carbon dioxide content in air exhaled by a patient are provided. Such system comprise a nasal cannula adapted to be connected to an anesthesia machine and a tube holder as described above.

BRIEF DESCRIPTION OF THE FIGURES

FIG. 5 presents a different embodiment of a device for attaching medical tube to a nasal cannula.

FIGS. 6 and 7 presents embodiments of a device for attaching medical tube to a nasal cannula having a bifurcated body.

DETAILED DESCRIPTION OF THE INVENTION

Figure 1:
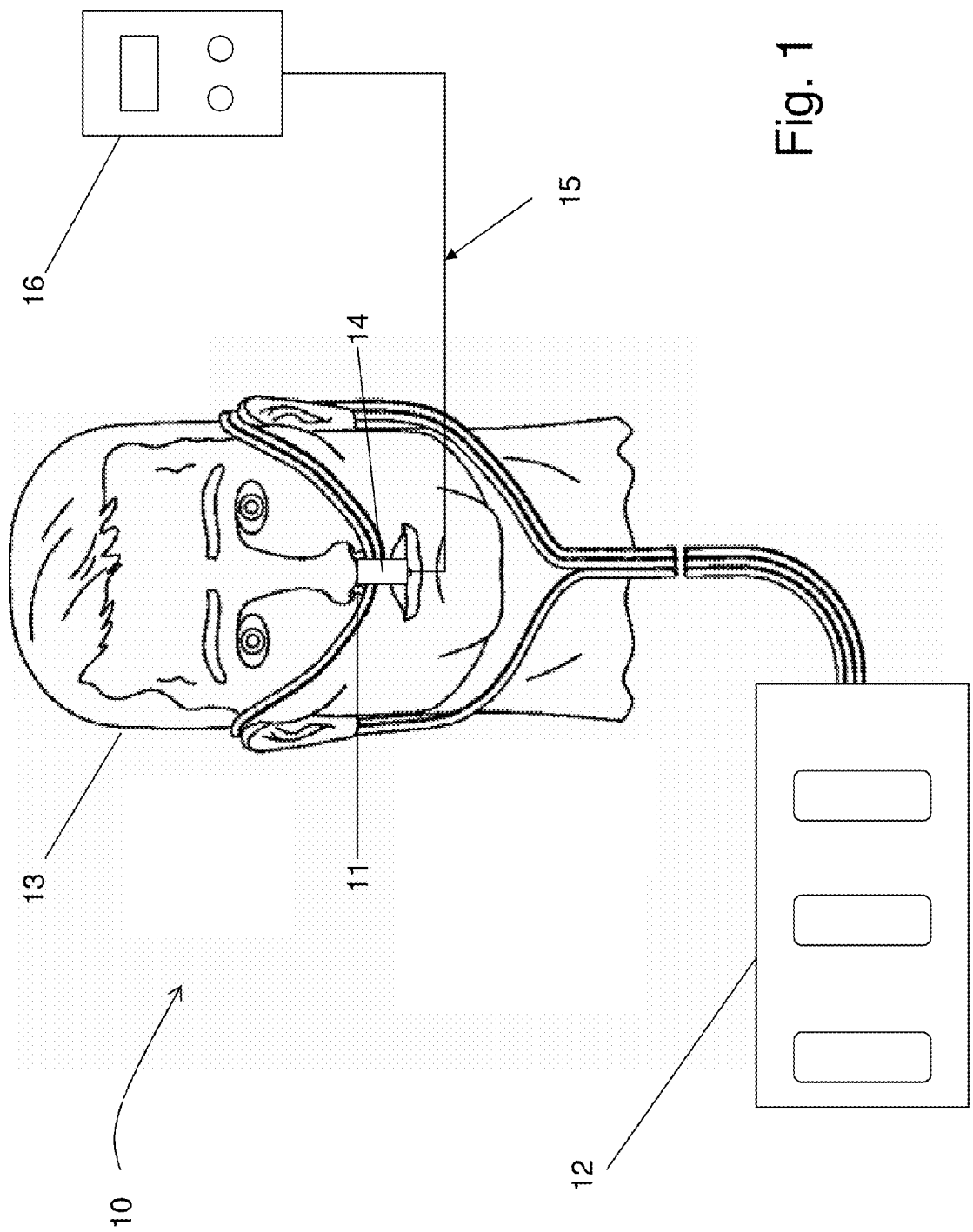
FIG. 1 presents a system for monitoring carbon dioxide content in air exhaled by a patient.

In one aspect, a system for monitoring carbon dioxide content in air exhaled by a patient is provided. Referring to FIG. 1, such system 10 includes a nasal cannula 11 adapted to be connected to an oxygen source 12 for supplying oxygen to the patient 13. Any type of nasal cannula known and used in the art may be employed. The system 10 also includes a device 14, described in more detail below, for attaching medical tubing 15 to a nasal cannula 11. Although, it is preferable that the device 14 releasably attaches to the nasal cannula, it may also be formed as an integral element of the cannula. The medical tubing 16 may be connected to a sensor 16, such as capnograph, that measures Carbon Dioxide content in the air exhaled by the patient.

In one embodiment, the device for attaching medical tubing to a nasal cannula may comprise a body having a distal end and a proximal end, at least one connector disposed on the body and adapted to releasably attach the body to the nasal cannula, and at least one tube holding member extending along at least one surface of the body and adapted to accept the medical tubing. The connector may comprise an elongated member and a pivot, such as a spring, that acts to engage the elongated member with the body, at lest one strap, at last one elastically biased clip, or combinations thereof. The tube holding member may comprise a receptacle set in a surface of the body, at least one loop positioned along a surface of the body, an adhesive strip positioned along a surface of the body, or a combination thereof. It should be noted that any embodiment of the connector may be combined with any embodiment of the tube holding member. The device may be formed from a variety of materials, including metal or plastic. In some embodiments, it may be desirable to re-use the device, and thus in such embodiments, the device may be made of material that can be easily sterilized.

Figure 2:
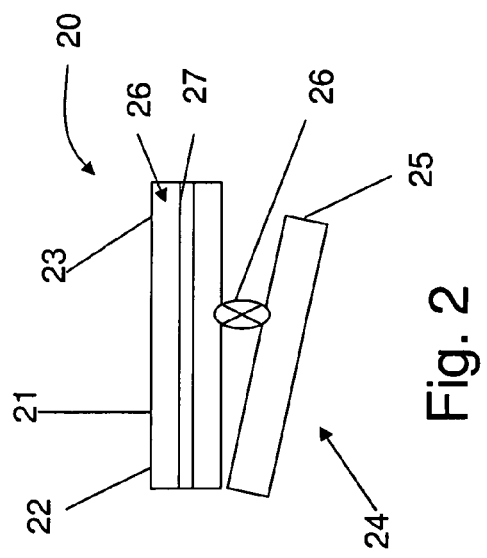

Referring to FIG. 2, the device 20 includes a body 21 having a distal end 22 and a proximal end 23. The connector 24 comprises an elongated member 25 and a pivot 26, such as a spring, that acts to engage the elongated member 25 with the body 21. Additionally, FIG. 2, shows the tube holding member 26 comprising a receptacle 27 set in the side surface of the body. Although the receptacle is shown only on the side surface of the body, additionally or alternatively, the receptacle may be located on the top surface of the body. Preferably, although unnecessary, the receptacle 26 may extend from the proximal end of the body to the distal end. The receptacle is adapted to accept a medical tubing, that is, the receptacle is preferably sized to avoid pinching the tubing while ensuring that the tube is held in place, such as by friction fit, during the procedure. In preferred embodiments, the receptacle is between about 0.05 and 0.3 inches wide and deep, and more preferably between about 0.12 and 0.216 inches wide and deep.

Figure 3:
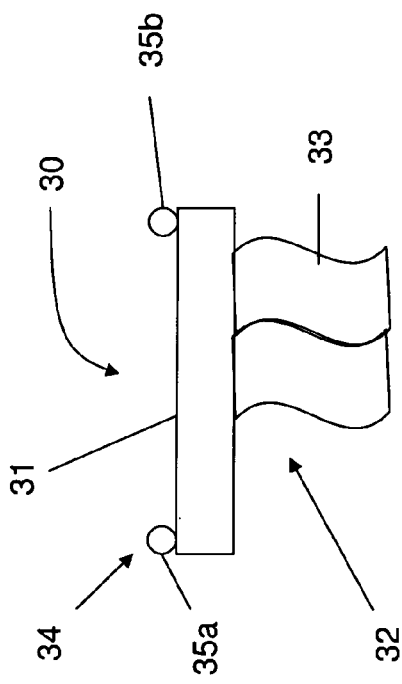
FIGS. 2-4 present various embodiments of a device for attaching medical tube to a nasal cannula.

In another embodiment, presented in FIG. 3, the device 30 includes a body 31 and a connector 32 comprising a strap 33. The strap may be made of plastic, fabric, nylon, latex, spandex, neoprene or any other materials capable of being shaped as a strap and used to attach the body to the nasal cannula. The strap may include hook-and-loop fasteners or any other fastening mechanism used and known in the art. In the embodiment of the device shown in FIG. 3, the tube holding member 35 comprises three loops 35a, 35b that are adapted to accept medical tubing without pinching it while ensuring that it effectively stays in place throughout the procedure. Although the device 30 is shown with 2 loops positioned on top surface at each end of the body, it will be understood that the specific position, including a particular surface and loop's position on that surface, and quantity of the loops may vary. Each loop may be a complete loop or, preferably, may have a gap or a gate through which the tube can be inserted into the loop. Additionally, while the loop is circular in the preferred embodiments, it may be of any other shape, such as elliptical, triangular, rectangular, that would efficiently hold the tubing stationary during the procedure without pinching it. In some embodiment, at least one of the loops may be capable of rotating about its base.

Figure 4:
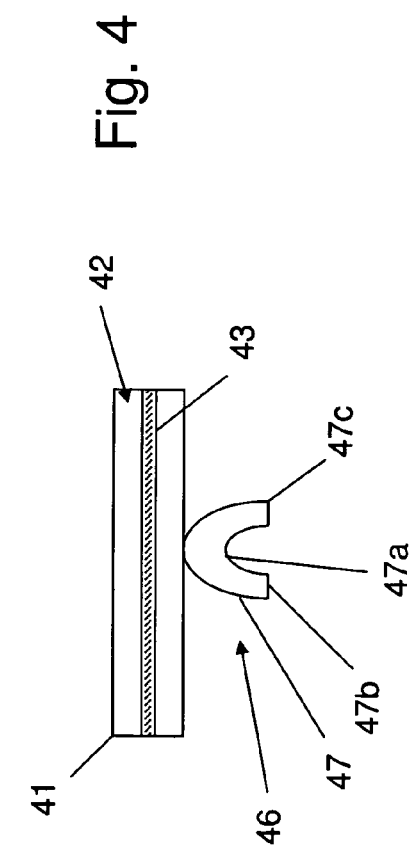

Yet another embodiment of the device for attaching medical tubing to a nasal cannula is shown in FIG. 4. In this embodiment, the device 40 includes a body 41 and a holding member 42 comprising an adhesive strip 43. Again, although the adhesive strip is shown along a side surface of the body, it may be positioned along any other surface of the body or several surfaces. The device 40 also includes a connector 46 comprising at least one clip 47 that is elastically biased to releasably attach the device to a nasal cannula. The clip 47 may comprise a body 47a having free ends 47b and 47c that are elastically biased toward each other. The shape of the body 47a preferably corresponds to the shape of the nasal cannula, and thus, the body 47a may be, for example, circular, rectangular, square, elliptical, and so forth. The clip may be made of any plastic or metal materials that possess sufficient amount of flexibility and elasticity to enable the free ends 47b, 47c of the clip 47 to be pulled apart while attaching the tube holder to the nasal cannula and to engage the nasal cannula when released.

In another embodiment, as shown in FIG. 5, a tube holder 50 may comprise a body 51 having a distal end 52 and a proximal end 53, a connector 54 disposed on the body 51 and adapted to releasably attach the body to the nasal cannula, and at least one body channel 55 extending through the body 51 and having outlets 55a, 55b at the distal end 52 and, optionally, at a proximal end 53, respectively. In essence, the difference between this embodiment and embodiments described above and shown in FIGS. 2-4 is that the holding member extending along at least one surface of the body is replaced with at least one channel cut through the body of the tube holder, while the body itself and the clip for attaching the body to the nasal cannula remain the same. In some embodiments, a medical tube 57 from a sensor 58, such as capnograph, may be fluidly connected to the channel 55 by a luer lock 58 or any other type of connector known and used in the art. Alternatively, the medical tube may simply be inserted into the channel. In the preferred embodiments, the channel's diameter is at least about 2 mm.

In yet other embodiments, as shown in FIG. 6, the body 61 of the tube holder 60 may be bifurcated at the distal end into a first prong 63 and a second prong 64. The prongs are spaced apart so they can be positioned in or near alternate nostrils of a patient. In embodiments with at least one channel through the body, the first prong 63 may comprise at least one first extension channel 65 extending through the first prong and the second prong 64 may comprise a second extension channel 66 extending through the second prong, with the first and second channel fluidly connected to the channel 67 through the body 61. The medical tube 68 may be fluidly connected to the channel 67 by a connector 69. Alternatively, the device may include two separate channels through the body with each channel being connected to one of the extension channels in the prongs.

Figure 7:
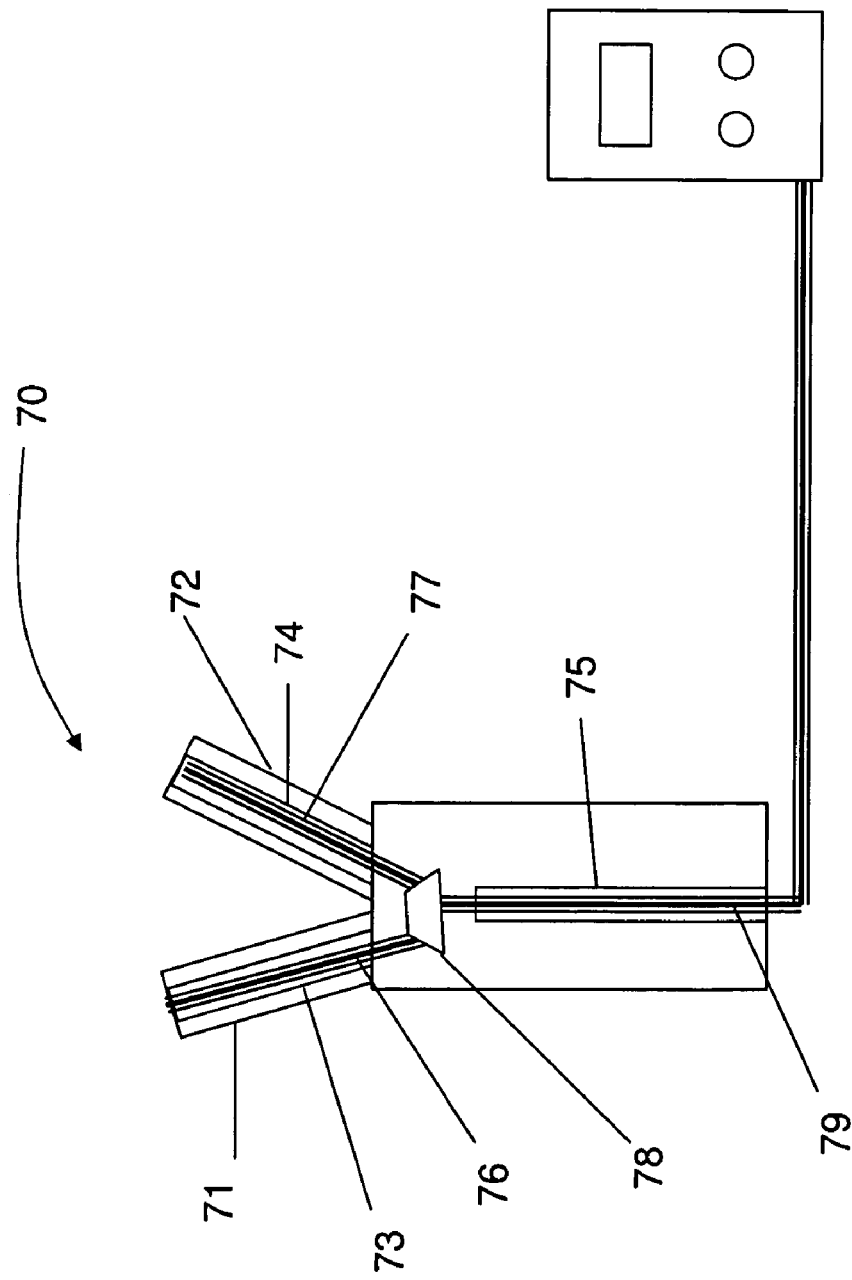

Referring to FIG. 7, in embodiments with at least one tube holding member extending along at least one side of the body, the first prong 71 may comprise at least one first tube extension member 73 extending along at least one side of the first prong and the second prong 72 may comprise at least one second tube extension member 74 extending along at least one side of the second prong. The extension members 73, 74 may be of the same or different type than each other or the holding member 75. In some embodiments, the tube holder may include medical tubes 76, 77 placed in extension members 73, 74 and a connector 78 that can fluidly connect these tubes 76, 77 to a medical tube 79, as described above, that can be placed into the holding member 75 of the body. Alternatively, a bifurcated tube may be used.

Note that the specifics embodiments are described in an exemplary manner and are not intended to limit the invention. In particular, infusion devices and needles manufactured of any acceptable material are contemplated to be within the scope of the invention, as are infusion devices and needles having varying design configurations and numbers of chambers and lumens. The scope of the invention is therefore defined in the claims which follow.

What is claimed is:

1. A device for attaching medical tubing to a nasal cannula, the device comprising:
    a body having a distal end and a proximal end;
    a connector disposed on the body and adapted to releasably attach the body to the nasal cannula; and
    at least one tube holding member extending along at least one surface of the body,
    wherein the body is bifurcated at the distal end into a first prong and a second prong, the first prong comprising at least one first tube extension member extending along at least one surface of the first prong, and the second prong comprising at least one second tube extension member extending along at least one surface of the second prong, and
    wherein the first prong and the second prong are spaced apart such that, when the body is attached to the nasal cannula, a first medical tube segment placed in the first tube extension member is positioned in or near one nostril of a patient and a second medical tube segment placed in the second extension member is positioned in or near the other nostril of the patient.

2. The device of claim 1, wherein the connector comprises an elongated member and a pivot that acts to engage the elongated member with the body.

3. The device of claim 1, wherein the connector comprises at least one strap.

4. The device of claim 1, wherein the connector comprises at least one elastically biased clip.

5. The device of claim 1, wherein the at least one tube holding member comprises a receptacle set in a surface of the body.

6. The device of claim 1, wherein the at least one tube holding member comprises at least one loop positioned along a surface of the body.

7. The device of claim 1, wherein the at least one tube holding member comprises an adhesive strip positioned along a surface of the body.

8. The device of claim 1, wherein the first medical tube segment and the second medical tube segment converge in the proximal direction for connection to a third medical tube segment placed in the at least one tube holding member.

\* \* \* \* \*